United States Patent [19]

Masaki et al.

[11] 4,155,932

[45] May 22, 1979

[54] METHOD FOR NON-CATALYTICALLY PRODUCING TERTIARY PHOSPHINE DICHLORIDES

[75] Inventors: Mitsuo Masaki, Chiba; Susumu Fuzimura, Ichihara, both of Japan

[73] Assignee: Ube Industries, Inc., Yamaguchi, Japan

[21] Appl. No.: 918,561

[22] Filed: Jun. 23, 1978

Related U.S. Application Data

[63] Continuation-in-part of Ser. No. 885,605, Mar. 13, 1978, Pat. No. 4,133,831.

[30] Foreign Application Priority Data

Mar. 18, 1977 [JP] Japan .................................. 52/29305

[51] Int. Cl.² .............................................. C07F 9/52
[52] U.S. Cl. ................................................ 260/543 P
[58] Field of Search ..................................... 260/543 P

[56] References Cited

FOREIGN PATENT DOCUMENTS 1192205 5/1965 Fed. Rep. of Germany.

OTHER PUBLICATIONS

Zeitschrift für an organishe and allgemeine Chemie. Band 369, pp. 33–37 (1969).
Chemical Abstr. vol. 75, col. 49,331(IV), (1971).
Mellor's Comprehensive Treatise on Inorganic and Theoretical Chemistry, vol. V, 963 (1961), Longurans.

*Primary Examiner*—Gerald A. Schwartz
*Attorney, Agent, or Firm*—Miller & Prestia

[57] ABSTRACT

Tertiary phosphine dichlorides are non-catalytically produced by directly reacting chlorine and carbon monoxide with a tertiary phosphine oxide preferably in a halogenated hydrocarbon solvent at a temperature of from −20° to 100° C.

12 Claims, No Drawings

METHOD FOR NON-CATALYTICALLY PRODUCING TERTIARY PHOSPHINE DICHLORIDES

The present application is a continuation-in-part of the copending application Ser. No. 885,605, filed on Mar. 13, 1978 now U.S. Pat. No. 4,133,831, granted Jan. 9, 1979.

The present invention relates to a method for producing tertiary phosphine dichlorides particularly, the present invention relates to a method for producing tertiary phosphine dichlorides in the absence of a catalyst.

The tertiary phosphine dichlorides are useful as intermediates for producing tertiary phosphine compounds which are useful as a reducing agent, and for producing tertiary phosphineimine compounds which are useful as an aminating agent. The tertiary phosphine dichlorides are also useful as a chlorinating agent.

It is publicly known that triphenylphosphine dichloride can be produced by reacting triphenylphosphine oxide with phosgene. It is also well known to produce the phosgene by a catalytic reaction of carbon monoxide with chlorine in the presence of a catalyst consisting of activated carbon or metal salt. Accordingly, it is anticipated that triphenylphosphine dichloride can be produced from carbon monoxide, chlorine and triphenylphosphine oxide by the combination of the above-mentioned method for producing phosgene from carbon monoxide and chlorine, with the afore-mentioned method for producing triphenylphosphine dichloride from phosgene and triphenylphosphine oxide. That is, the above-anticipated method contains two steps of chemical reactions. Especially, in the method for producing phosgene, carbon monoxide can react with chlorine only in the presence of the catalyst, such as activated carbon or metal salt, at a temperature of 60° to 150° C., under a pressure of 10 atmospheres or less. This reaction is exothermic. Therefore, it is difficult to maintain the reaction system at a predetermined temperature and reaction rate. In order to eliminate that difficulty, it is necessary to utilize a large scale complicated reaction apparatus, and carry out complicated reacting operations.

Under these circumstances, it is desirable to provide a convenient method for producing tertiary phosphine dichlorides in one single stage reacting operation, in the absence of a catalyst, without the above-mentioned disadvantages.

An object of the present invention is to provide a method for producing tertiary phosphine dichlorides in the absence of a catalyst.

Another object of the present invention is to provide a method for producing tertiary phosphine dichlorides in one single stage reacting operation.

A further object of the present invention is to provide a method for producing tertiary phosphine dichlorides at a relatively low temperature in a high yield.

The objects mentioned above can be attained by utilizing the method of the present invention, which process comprises directly reacting carbon monoxide and chlorine with a tertiary phosphine oxide.

The tertiary phosphine oxide usable for the process of the present invention can be selected from the compounds of the general formula (I):

wherein R, R$^1$ and R$^2$ respectively represent, independently from each other, a substituted or unsubstituted alkyl group having 1 through 18 carbon atoms, a substituted or unsubstituted cycloalkyl group having 5 to 10 carbon atoms or a substituted or unsubstituted aryl group having 6 through 14 carbon atoms. One or more of the groups R, R$^1$ and R$^2$ may have at least one substituent selected from the group consisting of chlorine and fluorine atoms, a cyano group and alkoxyl groups having 1 through 6 carbon atoms.

The direct reaction of the carbon monoxide and the chlorine with the tertiary phosphine oxide (I) is carried out in accordance with the chemical equation (III):

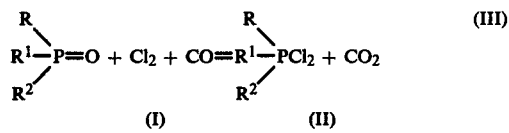

wherein R, R$^1$ and R$^2$ respectively represent, independently from each other, the same as that mentioned above. The resultant tertiary phosphine dichloride has the general formula (II) shown above.

The tertiary phosphine oxide compounds usable for the method of the present invention may be selected from, for example, the group consisting of trimethylphosphine oxide, triethylphosphine oxide, tripropylphosphine oxide, tributylphosphine oxide, methylethylbenzylphosphine oxide, trioctylphosphine oxide, methylbenzylphenylphosphine oxide, tricyclohexylphosphine oxide, tribenzylphosphine oxide, triphenylphosphine oxide, tolyldiphenylphosphine oxide, tris(chlorophenyl)phosphine oxide, tris(2-cyanoethyl)phosphine oxide, tris(fluorophenyl)phosphine oxide, tritolylphosphine oxide, butyldiphenylphosphine oxide, cyclohexyl-diphenylphosphine oxide, dicyclohexylphenylphosphine oxide, diethylphenylphosphine oxide, dimethylphenylphosphine oxide, ethyldiphenylphosphine oxide, dimethylchloromethylphosphine oxide, methylethylbutylphosphine oxide, tris(trifluoromethyl)phosphine oxide and tris(2-fluoroethyl)phosphine oxide.

The chlorine and carbon monoxide are not limited to a special grade thereof, respectively. In the method of the present invention, the tertiary phosphine oxide, chlorine and carbon monoxide are respectively used in any amounts as long as the amounts can satisfy stoichiometrically the above-mentioned equation (I). In the case where the tertiary phosphine oxide is used in a stoichiometrically excessive amount to the amount of chlorine used, the tertiary phosphine dichloride is produced in a stoichiometrical corresponding to the amount of the chlorine used. Also, in the case where the chlorine is used in a stoichiometrically excessive amount to the amount of the tertiary phosphine oxide used, the resultant tertiary phosphine dichloride is obtained in a stoichiometrical amount corresponding to the amount of the tertiary phosphine oxide. However, the later case is not economical because it is difficult to completely recover the excessive amount of the chlorine from the reaction mixture.

The carbon monoxide is usually used in the state of a gas in the process of the present invention. In this case, the carbon monoxide gas is satisfactorily used under an ambient pressure or a slightly pressurized condition. In order to shorten the time necessary to complete the reaction, it is preferable that the carbon monoxide gas in the reaction mixture be maintained at a pressure of from 5 to 100 atmospheres. The reaction can be effected even under a pressure of more than 100 atmospheres. However, such a high pressure has no merit with regard to the reaction.

The method of the present invention may be effected in a solvent not reactive to the reaction mixture or without using any solvent. When the tertiary phosphine oxide and the resultant tertiary phosphine dichloride are in the state of a solid, it is preferable to utilize a solvent for the reaction of the present invention, because the reaction components can be homogeneously mixed in the solvent and, therefore, reaction can be carried out smoothly. The solvent may be selected from conventioned solvent compounds which are non-reactive to the reaction components and the resultant product under the reaction conditions in the process of the present invention. For example, the solvent may be selected from liquid halogenated hydrocarbons, for example, tetrachloromethane, 1,1,2,2-tetrachloroethane, fluorotrichloromethane and 1,1,2-trichloro-1,2,2-trifluoroethane.

If a non-halogenated liquid hydrocarbon, for example, hexane, haptane or octane, is used for the process of the present invention, the hydrocarbon is chlorinated with chlorine before the start of or during the process of the present invention, and the resultant chlorinated hydrocarbon act as a solvent for the process of the present invention. In the case where the reaction of the process of the present invention is carried out in the dark, aromatic hydrocarbons, for example, benzene and toluene or chlorinated aromatic hydrocarbons, for example, dichlorobenzene, can be used as a solvent. This is because the above-mentioned aromatic hydrocarbons or chlorinated aromatic hydrocarbons are not chlorinated in the dark.

In the method of the present invention, the reaction temperature is not limited to a special range. However, it is preferable that the reaction temperature be in a range of from $-20°$ to $100°$ C., more preferably, from $0°$ to $60°$ C. Even if the reaction temperature is lower than $-20°$ C., the reaction can be effected. However, the lower the reaction temperature, the lower the reaction velocity. Therefore, it is preferable that the reaction temperature not be lower than $-20°$ C. Also, even if the reaction temperature is higher than $100°$ C., it is possible to produce the tertiary phosphine dichlorides. However, it should be noted that the higher than $100°$ C. the reaction temperature is, the higher the degree of decomposition of the resultant tertiary phosphine dichloride. The decomposition results in a low yield of the product. Therefore, it is preferable that the reaction temperature not be higher than $100°$ C.

The velocity of the reaction of the process of the present invention is variable, depending on the type of the tertiary phosphine oxide used as a reaction component, particularly, the types of the substituents R, $R^1$ and $R^2$ in the formula (1). In some types of R, $R^1$ and $R^2$, the reaction can be smoothly effected even at a room temperature. In this case, no heating of the reaction mixture is necessary. In other types of R, $R^1$ and $R^2$, the reaction mixture is preferably heated to accelerate the reaction. Since the reaction in the process of the present invention is an exothermic reaction, the temperature of the reaction mixture may increase with the progress of the reaction when a solvent is used in an improper amount and the scale of the process is improperly large. In this case, it is necessary to cool the reaction mixture to a predetermined temperature.

The resultant tertiary phosphine dichloride has a great tendency to be easily hydrolized. That is, when brought into contact with water, the tertiary phosphine dichloride is decomposed so as to form tertiary phosphine oxide and hydrogene chloride. Accordingly, it is necessary to carry out the reaction of the process of the present invention in an anhydrous condition.

In the method of the present invention, the method for bringing the tertiary phosphine oxide, chlorine and carbon monoxide into contact with each other, is not limited to a special method as long as the contact can be effectively carried out. For example, a solution containing the tertiary phosphine oxide and chlorine may be shaken in a carbon monoxide atmosphere so as to effect the reaction in the process of the present invention.

The tertiary phosphine dichloride can be isolated by removing the non-reacted materials and, optionally, the solvent from the reaction mixture. However, as stated above, the tertiary phosphine dichloride has a tendency to be easily hydrolized. Accordingly, it is preferable that the reaction mixture be usually utilized in a desired next reaction process without isolating the resultant tertiary phosphine dischloride from the reaction mixture. For example, in the case where a tertiary phosphine imine is prepared from a corresponding tertiary phosphine dichloride and an amine or ammonia, the amine or ammonia may be admixed into the reaction product obtained by the process of the present invention, or the reaction product obtained by the process of the present invention may be brought into contact with the amine or ammonia. Also, in the case where a carboxylic acid is converted into a carboxylic acid chloride, the carboxylic acid may be mixed with the reaction product of the process of the present invention and the mixture may be heated to a reaction temperature. Furthermore, in the case where a tertiary phosphine compound is produced by the reduction of a corresponding tertiary phosphine dichloride, the reaction product obtained by the process of the present invention may be subjected to the above-mentioned reduction process. If the reaction product obtained by the process of the present invention contains a solvent which is reactive to the reduction process, it is necessary to substitute the reactive solvent by another solvent which is not reactive to the reduction process before the reduction process.

The tertiary phosphine dichloride obtained by the process of the present invention has the general formula (II), and includes, for example, trimethylphosphine dichloride, triethylphosphine dichloride, tripropylphosphine dichloride, tributylphosphine dichloride, methylethylbenzylphosphine dichloride, trioctylphosphine dichloride, methylbenzylphenylphosphine dichloride, tricyclohexylphosphine dichloride, tribenzylphosphine dichloride, triphenylphosphine dichloride, tolyldiphenylphosphine dichloride, tris(chlorophenyl)phosphine dichloride, tris(2-cyanoethyl)phosphine dichloride, tris(fluorophenyl)phosphine dichloride, tritolylphosphine dichloride, butylphenylphosphine dichloride, cyclohexyldiphenylphosphine dichloride, dicyclohexylphenylphosphine dichloride diethylphenylphosphine dichloride, dimethylphenylphosphine dichloride, ethyldiphenylphosphine dichloride, dimethylchloromethylphosphine dichloride, methylethylbutylphosphine dichloride, tris(trifluoromethyl)phosphine dichloride and tris(2-fluoroethyl)phosphine dichloride.

The method of the present invention is very effective for producing, in one step, tertiary phosphine dichloride in a high yield only by admixing the corresponding tertiary phosphine oxide with chlorine and carbon monoxide without using a catalyst. The resultant tertiary phosphine dichlorides are valuable as a material for industrially producing tertiary phosphines tertiary phosphine imines or acid chlorides.

Hereinafter, the present invention is illustrated in detail by examples. In the examples, the yield and percent selectivity of the resultant tertiary phosphine dichloride were determined either by Method A in which the tertiary phosphine dichloride was reduced to convert it to the corresponding tertiary phosphine, by Method B wherein the tertiary phosphine dichloride was converted into the corresponding tertiary phosphine imine, by Method C wherein the tertiary phosphine dichloride was reacted with a carboxylic acid so as to produce a carboxylic acid chloride. Methods A, B and C are explained in detail below.

Method A:

A reaction product containing the resultant tertiary phosphine dichloride is distilled under atmospheric pressure to recover the solvent from the reaction product. The distillation residue is dissolved in toluene. The solution thus prepared is placed in an autoclave. After closing the autoclave, hydrogen gas is fed into the autoclave under pressure. The autoclave is heated and maintained at a temperature of from 160° to 180° C., under a pressure of about 100 kg/cm$^2$, for 90 to 120 minutes, while shaking it, so as to convert the tertiary phosphine dichloride into the corresponding tertiary phosphine. This conversion is carried out completely. After the completion of the conversion, the reaction mixture in the autoclave is neutralized by adding an aqueous solution of hydrogen sodium carbonate. The toluene fraction is separated from the reaction mixture. The amount of the tertiary phosphine in the toluene fraction is determined by means of gas chromatography. The yield of the tertiary phosphine dichloride in the reaction product is calculated from the above-determined amount of the tertiary phosphine.

Method B:

A reaction product containing a tertiary phosphine dichloride is mixed with aniline in an amount equivalent in mole to the theoretical amount of the tertiary phosphine dichloride in the reaction product and with triethylamine in an amount of twice that of the aniline, while cooling with ice and stirring the mixture. The mixture is slowly heated to a temperature of 25° C. and, thereafter, stirred at this temperature for one hour so as to completely convert the tertiary phosphine dichloride into the corresponding tertiary phosphine imine. The reaction mixture is filtered and the filtrate was washed with water to remove the resultant hydrochloric salt of triethylamine from the reaction mixture. The remaining filtrate is subjected to the isolation of the tertiary phosphine imine. The amount of the isolated tertiary phosphine imine is determined by means of gas chromatography. The yield of the tertiary phosphine dichloride in the reaction product is calculated from the above-determined amount of the tertiary phosphine dichloride.

Method C:

A reaction product containing a tertiary phosphine dichloride is mixed with 2,4-dichlorobenzoic acid in an amount equivalent in mole to the theoretical amount of the tertiary phosphine dichloride in the reaction product. The mixture is heated to a refluxing temperature of the solvent in the mixture and maintained at this temperature for 3.5 hours while stirring, so as to allow the tertiary phosphine dichloride to react with the 2,4-dichlorobenzoic acid. During the reaction, the generated hydrogen chloride gas is removed from the reaction mixture. After the completion of the reaction, methyl alcohol and triethylamine, each in an amount equivalent in mole to the theoretical yield of the resultant 2,4-dichlorobenzoic acid chloride, are admixed into the reaction product, so as to convert the resultant 2,4-dichlorobenzoic acid chloride into a methylester of the 2,4-dichlorobenzoic acid. The amount of the methylester of 2,4-dichlorobenzoic acid is determined by means of gas chromatography. The amount of the tertiary phosphine dichloride in the reaction product is calculated from the above-determined amount of the methylester of 2,4-dichlorobenzoic acid.

EXAMPLES 1 THROUGH 7

In Example 1, a glass reaction vessel was charged with 10.2 m mole of tributylphosphine oxide and 15 ml of tetrachloromethane. The mixture in the vessel was admixed with 10.2 m mol of liquid chlorine. A homogeneous yellow solution was obtained. The reaction vessel containing the above-prepared solution was placed in an autoclave. The inside space of the autoclave was filled with carbon monoxide under a pressure of 30 kg/cm$^2$. The autoclave was shaken at a temperature of 25° C., for 30 minutes, so as to allow the solution and the carbon monoxide to contact each other. After the reaction was completed, it was observed that the yellow color of the solution was completely lost. The yield of the resultant tributylphosphine dichloride was determined by Method A. The results are shown in Table 1.

In each of the Examples 2 through 7, the same procedures as those in Examples were carried out, except that the types and amounts of the materials, and the solvent used, the reaction temperature and time, the type of tertiary phosphine dichloride obtained and the type of the analytical method applied were those shown in Table 1. The results are shown in Table 1.

Table 1

| | Reaction Conditions | | | | | | | |
|---|---|---|---|---|---|---|---|---|
| | Tertiary Phosphine Oxide | | Chlorine | Carbon Monoxide | Solvent | | Temperature (° C.) | Time (minute) |
| Example No. | Type | Amount (m mol) | Amount (m mol) | Pressure (kg/cm$^2$) | Type | Amount (ml) | | |
| 1 | Tributyl Phosphine | 10.2 | 10.2 | 30 | tetrachloromethane | 15 | 25 | 30 |

Table 1-continued

| Example No. | | | | | | | | |
|---|---|---|---|---|---|---|---|---|
| 2 | oxide " | 10.0 | 10.0 | 60 | (*) | 15 | 25 | 10 |
| 3 | " | 10.0 | 10.0 | 60 | tetrachloromethane | 50 | 25 | 10 |
| 4 | " | 10.0 | 10.0 | 10 | " | 20 | 12 | 120 |
| 5 | Triethyl Phosphine oxide | 20.0 | 20.0 | 60 | " | 15 | 25 | 30 |
| 6 | Trioctyl Phosphine oxide | 10.0 | 10.0 | 60 | " | 15 | 25 | 20 |
| 7 | Triphenyl Phosphine oxide | 11.7 | 11.7 | 60 | " | 15 | 60 | 60 |
|   |   |   |   |   |   |   | 100 | 90 |

Note:
* 1,1,2-trichloro-1,2,2-trifluroethane

| Example No. | Product Type | Analytical Method | Yield (%) |
|---|---|---|---|
| 1 | Tributylphosphine Dichloride | A | 87 |
| 2 | " | A | 90 |
| 3 | " | B | 94 |
| 4 | " | C | 81 |
| 5 | Triethylphosphine Dichloride | A | 58 |
| 6 | Trioctylphosphine Dichloride | A | 92 |
| 7 | Triphenylphosphine Dichloride | A | 86 |

What we claim is:

1. A method for non-catalytically producing a tertiary phosphine dichloride comprising directly reacting chlorine and carbon monoxide with a tertiary phosphine oxide of the formula (I):

wherein R, R¹ and R² respectively represent, independently from each other, a substituted or unsubstituted alkyl group having 1 through 18 carbon atoms, a substituted or unsubstituted cycloalkyl group having 5 to 10 carbon atoms or a substituted or unsubstituted aryl group having 6 through 14 carbon atoms; and wherein, when substituted, one or more of said groups R, R¹ and R² have at least one substituent selected from the group consisting of chlorine and fluorine atoms, a cyano group and alkoxy groups having 1 through 6 carbon atoms.

2. A method as claimed in claim 1, wherein said tertiary phosphine oxide is selected from the group consisting of trimethylphosphine oxide, triethylphosphine oxide, tripropylphosphine oxide, tributylphosphine oxide, methylethylbenzylphosphine oxide, trioctylphosphine oxide, methylbenzylphenylphosphine oxide, tricyclohexylphosphine oxide tribenzylphosphine oxide, triphenylphosphine oxide, tolyldiphenylphosphine oxide, tris(chlorophenyl)phosphine oxide, tris(2-cyanoethyl)phosphine oxide, tris(fluorophenyl)phosphine oxide, tritolylphosphine oxide, butyldiphenylphosphine oxide, cyclohexyldiphenylphosphine oxide, dicyclohexylphenylphosphine oxide, diethylphenylphosphine oxide, dimethylphenylphosphine oxide, ethyldiphenylphosphine oxide, dimethylchloromethylphosphine oxide, methylethylbutylphosphine oxide, tris(trifluoromethyl)phosphine oxide and tris(2-fluoroethyl)phosphine oxide.

3. A method as claimed in claim 1, wherein the carbon monoxide in the reaction mixture has a pressure of from 1 to 100 atmospheres.

4. A method as claimed in claim 1, wherein said reaction is carried out in a halogenated hydrocarbon solvent which is not reactive to the reaction mixture.

5. A method as claimed in claim 1, wherein said solvent is selected from the group consisting of tetrachloromethane, fluorotrichloromethane, 1,1,2-trichloro-1,2,2-trifluoroethane and 1,1,2,2-tetrachloroethane.

6. A method as claimed in claim 1, wherein said reaction is carried out at a temperature of from −20° to 100° C.

7. A method for non-catalytically producing a tertiary phosphine dichloride comprising directly reacting chlorine and carbon monoxide with a tertiary phosphine oxide of the formula (I):

wherein R, R¹ and R² respectively represent, independently from each other, a substituted or unsubstituted alkyl group having 1 through 18 carbon atoms, or a substituted or unsubstituted cycloalkyl group having 5 to 10 carbon atoms, and wherein, when substituted, one or more of said groups R, R¹ and R² have at least one substituent selected from the group consisting of chlorine and fluorine atoms, a cyano group and alkoxyl groups having 1 through 6 carbon atoms.

8. A method as recited in claim 7 wherein said tertiary phosphine oxide is selected from the group consisting of trimethylphosphine oxide, triethylphosphine oxide, tripropylphosphine oxide, tributylphosphine oxide, trioctylphosphine oxide, tricyclohexylphosphine oxide, tris (2-cyanoethyl) phosphine oxide, dimethylchloromethylphosphine oxide, methylethylbutylphosphine oxide, tris (trifluoromethyl) phosphine oxide and tris (2-fluoroethyl) phosphine oxide.

9. A method as claimed in claim 7, wherein the carbon monoxide in the reaction mixture has a pressure of from 1 to 100 atmospheres.

10. A method as claimed in claim 7, wherein said reaction is carried out in a halogenated hydrocarbon solvent which is not reactive to the reaction mixture.

11. A method as claimed in claim 7, wherein said solvent is selected from the group consisting of tetrachloromethane, fluorotrichloromethane, 1,1,2-trichloro-1,2,2-trifluoroethane and 1,1,2,2-tetrachloroethane.

12. A method as claimed in claim 7, wherein said reaction is carried out at a temperature of from −20° to 100° C.

* * * * *

UNITED STATES PATENT AND TRADEMARK OFFICE
CERTIFICATE OF CORRECTION

PATENT NO. : 4,155,932
DATED : May 22, 1979
INVENTOR(S) : Mitsuo Masaki et al

It is certified that error appears in the above-identified patent and that said Letters Patent are hereby corrected as shown below:

Page One, Item #73, delete "Ube Industries, Inc." and substitute therefor --Ube Industries, Ltd.--.

Signed and Sealed this

Twenty-fifth Day of September 1979

[SEAL]

Attest:

LUTRELLE F. PARKER
*Attesting Officer*     *Acting Commissioner of Patents and Trademarks*